(12) United States Patent
Cheng

(10) Patent No.: US 10,548,936 B2
(45) Date of Patent: Feb. 4, 2020

(54) METHOD FOR REDUCING WEIGHT

(71) Applicant: Nanzheng Cheng, Foster City, CA (US)

(72) Inventor: Nanzheng Cheng, Foster City, CA (US)

( * ) Notice: Subject to any disclaimer, the term of this patent is extended or adjusted under 35 U.S.C. 154(b) by 158 days.

(21) Appl. No.: 15/499,380

(22) Filed: Apr. 27, 2017

(65) Prior Publication Data

US 2018/0311295 A1    Nov. 1, 2018

(51) Int. Cl.
*A61K 36/54*    (2006.01)
*A61K 36/481*   (2006.01)
*A61K 36/48*    (2006.01)
*A61K 36/00*    (2006.01)

(52) U.S. Cl.
CPC ............ *A61K 36/54* (2013.01); *A61K 36/481* (2013.01); *A61K 2236/331* (2013.01)

(58) Field of Classification Search
None
See application file for complete search history.

(56) References Cited

U.S. PATENT DOCUMENTS 6,200,569 B1    3/2001    Cheng
9,089,577 B1    7/2015    Cheng

FOREIGN PATENT DOCUMENTS

| CN | 102068589 A | | 5/2011 | |
|---|---|---|---|---|
| CN | 105267780 A | * | 1/2016 | |
| CN | 105853877 A | | 8/2016 | |
| CN | 106177798 A | | 12/2016 | |
| KR | 2011030973 A | * | 3/2011 | |
| WO | WO-2016007106 A2 | * | 1/2016 | ........... A61K 31/205 |

* cited by examiner

*Primary Examiner* — Michael Barker
*Assistant Examiner* — Randall Winston
(74) *Attorney, Agent, or Firm* — Perkins Coie LLP; Viola T. Kung

(57) ABSTRACT

This invention relates to methods and compositions for reducing excessive body weight from a mammal subject suffering from excessive weight or overt obesity. The invention also relates to a method for preventing a mammal at risk for gaining excessive weight. The methods comprise administering to a subject effective amounts of active ingredients consisting essentially of a water extract of cinnamon and a water extract of Radix Astragali.

8 Claims, 2 Drawing Sheets

METHOD FOR REDUCING WEIGHT

TECHNICAL FIELD

This invention relates to a method for reducing excessive body weight from a mammal subject or for preventing a mammal at risk for gaining excessive body weight. The method comprising administering a water extract of cinnamon and a water extract of Radix Astragali to a subject in need thereof.

BACKGROUND OF THE INVENTION

Obesity is a medical condition in which excess body fat has accumulated to the extent that it may have an adverse effect on health, leading to reduced life expectancy and/or increased health problems. Body mass index (BMI), a measurement which compares weight and height, defines individuals as overweight or as suffering from excessive body weight (pre-obese) if their BMI is between 25 and 30 $kg/m^2$, and overtly obese when their BMI is greater than 30 $kg/m^2$. There is increased risk of co-morbidities for individuals with a BMI between 25.0 to 29.9, and moderate to severe risk of co-morbidities for individuals with a BMI greater than 30. Obesity is a serious health and economic burden, and predisposes an individual to a variety of cardiometabolic diseases. Obesity increases the likelihood of metabolic syndrome, hypertension, type 2 diabetes, non-alcoholic fatty liver disease, or obesity-related kidney disease.

U.S. Pat. No. 6,200,569 discloses that water extract of cinnamon is effective to treat diabetes.

U.S. Pat. No. 9,089,755 discloses that combined administration of a water extract of cinnamon and a water extract of Radix Astragali provides an enhanced insulin sensitivity and/or insulin-like action.

There exists a need for a method that is safe and can effectively reduce or prevent weight gain in a person in need thereof.

DETAILED DESCRIPTION OF THE INVENTION

Figure 1:
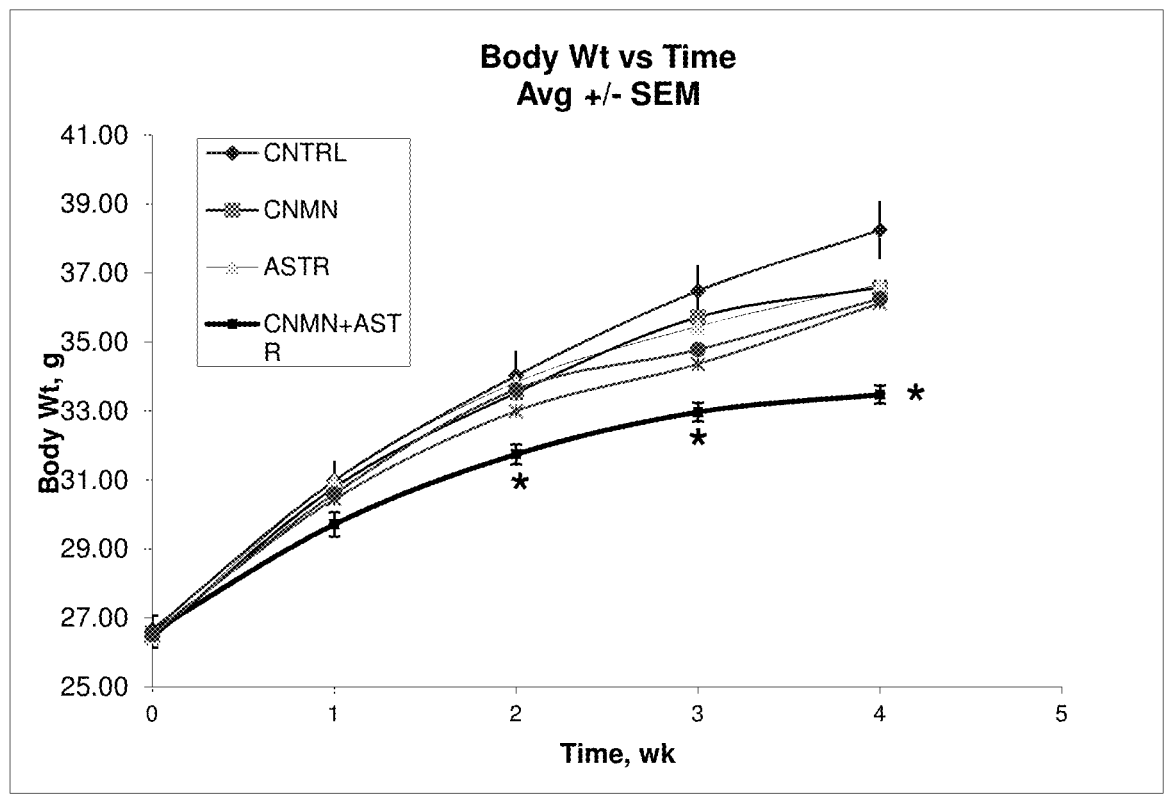
FIG. 1 shows the mean body weight vs. time at week 0, 1, 2, 3, and 4 of each group of mice having different diets. Mice having high fat diets supplemented with 0.1% cinnamon extract and 0.1% astragalus extract had significantly less body weight comparing with control (*) at weeks 2, 3, and 4, by unpaired t-tests.

The present invention is directed to a method for reducing excessive body weight from a subject. The method comprises the steps of identifying a subject suffering from excessive weight or overt obesity, and administering to the subject effective amounts of water extracts of cinnamon and Radix Astragali. A human subject suffering from excessive body weight (pre-obese) is defined by a Body Mass Index (BMI) between 25 and 30 $kg/m^2$ and a human subject suffering from overt obesity is defined by BMI greater than 30 $kg/m^2$. The combination of water extracts of cinnamon and Radix Astragali effectively reduces excessive body weight of a pre-obese subject or an overtly obese subject.

The present invention is also directed to a method for treating obesity. The method comprises the steps of identifying a subject suffering from overt obesity, and administering to the subject effective amounts of water extracts of cinnamon and Radix Astragali, whereby the excessive body weight of the subject is reduced.

The present invention is further directed to a method for preventing weight gain in a subject at risk for gaining excessive weight, comprising the steps of identifying a subject in need thereof, and administering to the subject effective amounts of water extracts of cinnamon and Radix Astragali. Subjects at risk for gaining excessive weight include pre-obese subjects, overt obese subjects, or subjects having high calorie diets or high fat diets.

The inventor has discovered that combined administration of a water extract of cinnamon and a water extract of Radix Astragali provides a beneficial effect of reducing weight or reducing weight gain. The inventor has discovered that combined administration of a water extract of cinnamon and a water extract of Radix Astragali provides a better activity of reducing weight; or preventing or reducing weight gain. In one embodiment, combined administration of a water extract of cinnamon and a water extract of Radix Astragali provides at least an additive effect. In a preferred embodiment, combined administration of a water extract of cinnamon and a water extract of Radix Astragali provides a synergistic effect.

In one embodiment, the method comprises administering to a subject an effective amount of a water extract of cinnamon and an effective amount of a water extract of Radix Astragali. "An effective amount," as used herein, refers to an amount that is effective to reduce weight, or preventing or reducing weight gain in a subject. In one embodiment, this method does not contain a step of administering to a subject an additional active ingredient (other than cinnamon or Radix Astragali) that is known to reduce weight of a subject. The two water extracts cinnamon and Radix Astragali can be administered simultaneously in one composition or in two separate compositions. Alternatively, the two water extracts can be administered sequentially.

In another embodiment, the method comprises administering to a subject active ingredients consisting essentially of an effective amount of a water extract of Cinnamon and an effective amount of a water extract of Radix Astragali, wherein said water extracts are administered in amounts effective to reduce weight in a subject in need thereof. "Consisting essentially of", as used herein, refers that the active ingredients only contain cinnamon and Radix Astragali, and do not contain any other active ingredient that is known to reduce weight.

The weight ratio of the water extract of cinnamon and the water extract of Radix Astragali used in the present methods is in general from about 5:1 to 1:5, or 3:1 to 1:3; with about 2:1 to 1:2 being preferred. About equal weight ratio (1:1) of cinnamon to Radix Astragali is more preferred. "About" as used herein, refers to ±10% of the recited value.

The present invention is useful for mammalian subjects, such as humans, dogs and cats. The present invention is particularly useful for humans.

Preferred source of a raw material of cinnamon is bark from a cinnamon tree, in the family of Cinnamomum. Preferred species are *Cinnamomum mairei, Cinnamomum zeylanicum, Cinnamomum burmannii,* and *Cinnamomum cassia. Cinnamomum mairei* is a tree with highly aromatic bark; its bark can be used for preparing extracts. Commercial Cinnamomum bark, which is the dried inner bark of the shoots, and ground cinnamon obtained from a grocery store can also be used for preparing water extracts.

Radix Astragali is the dried root of perennial herbs, *Astragalus membranaceus* (Fisch.) Bunge and *Astragalus mongholicus* Bunge (Fabaceae). Radix Astragali is also named *Astragalus* root, *Astragalus propinquus*, huang-chi, huangqi, hwanggi, membranous milkvetch, milkvetch, Mongolian milk-vetch, neimeng huangqi, ogi, ougi, zhongfengnaomaitong. Major chemical constituents in Radix Astragali are triterpene saponins (astragalosides I-X and isoastragalosides I-IV), and polysaccharides (e.g. astragalan, astraglucan AMem-P)

Cinnamon and Radix Astragali used in this invention are natural substances derived from herbs, and are safe for human consumption.

Water extracts of Cinnamon and Radix Astragali can be prepared according to the procedures described in U.S. Pat. No. 6,200,569, which is incorporated herein by reference in its entirety. In brief, the source tissue is obtained either as a ground powder or is prepared by cutting the plant tissue into small pieces, pulverizing it, grinding it or otherwise increasing the surface area of the pieces of tissue to facilitate extraction. Hydrophilic solvents such as water are used for extraction. Because it is safe, easy to use, and economic, water is a preferred solvent for extraction. A small amount of buffer can be added to water to maintain the pH. A small amount of ethanol or methanol also can be added to water as a solvent for extraction. The amount of solvent added to the raw material for extraction is, in general, in a volume ranging from 2-200 times per unit weight of the raw material, and preferably 20-100 times per unit weight.

Other solvents which can be used include dilute acids and bases. Dilute acids, such as acetic acid and hydrochloric acid also can be used: the acid concentration should be less than about 1 N, and preferably less than 0.5 N. For example, 0.1 N acetic acid or 0.1 N hydrochloric acid can be an effective solvent. Dilute bases, for example, ammonium hydroxide or sodium hydroxide, can be used as a solvent; the concentration of the base should be less than about 1 N and preferably less than 0.5 N. For example, 0.1 N $NH_4OH$ can be used to prepare the extract.

The extraction can be performed at a wide range of temperatures, but preferably at a temperature range from room temperature to about 100° C., from about 15 minutes to overnight.

After extraction, the liquid which contains the activity is separated from any solid debris by centrifugation or filtration. If acid or base is used as the solvent for extraction, the extract usually is neutralized before further usage.

The water extract, which is free of solid debris, can be used directly, or the water extract can be lyophilized or dried to form a powder. The liquid or the powder can be incorporated into a variety of basic materials in the form of a liquid, powder, tablets, or capsules.

While it is possible for the water extracts of cinnamon and Radix Astragali to be administered alone without other excipients, it is preferable to formulate the active ingredients as a pharmaceutical or neutraceutical formulation. For example, the formulation may include diluents or excipients such as fillers, binders, wetting agents, disintegrators, surface-active agents, lubricants and the like. Typical unit dosage forms include tablets, pills, powders, solutions, suspensions, emulsions, granules, capsules, suppositories. Each carrier is compatible with other ingredients in the formulation and is biologically acceptable to the subject and inert.

Formulations include those suitable for oral and parenteral (including subcutaneous, intramuscular, intravenous and intradermal) administration, with oral formulations being preferred. A preferred oral formulation is an encapsulated dry powder of a water extract of cinnamon, a water extract of Radix Astragali, or a mixture of both water extracts.

The formulations can be conveniently prepared in unit dosage form and can be prepared by any method known in the art.

For example, to prepare formulations suitable for injection, solutions and suspensions are sterilized and are preferably isotonic to blood. In making injectable preparations, carriers which are commonly used in this field are used, for example, water, ethyl alcohol, propylene glycol, ethoxylated isostearyl alcohol, polyoxylated isostearyl alcohol, polyoxyethylene sorbitol and sorbitate esters. In these instances, adequate amounts of isotonicity adjusters such s sodium chloride, glucose or glycerin can be added to make the preparations isotonic. The aqueous sterile injection solutions may further comprise oxidants, buffers, bacteriostats, and like additions acceptable for parenteral formulations.

The formulation according to the invention can be administered by any suitable routes, including oral and parenteral (including intraperitoneal, subcutaneous, intramuscular, intravenous and intradermal) routes. It will be appreciated that the preferred route will vary with the condition and age of the patient, and how long-lasting the treatment is.

Effective amounts of active ingredients will vary depending upon several factors, including, but not limited to, the age and weight of the patient, the type of the disease state treated, how advanced the disease state is, the general health of the patient, the severity of the symptoms, whether the water extract of cinnamon and the water extract of Radix Astragali are administered alone or in combination with other active ingredients, the incidence of side effects, and the like. Generally, a human subject may take 1-10 capsules containing the water extract of cinnamon and the water extract of Radix Astragali for treatment. Each capsule contains 100-1000 mg of dry powder of a water extract of cinnamon alone, a water extract of Radix Astragali alone, or a mixture thereof. Preferred daily use in a human subject is 500-5000 mg total of water extracts of cinnamon and Radix Astragali. When a capsule contains a mixture of a water extract of cinnamon and a water extract of Radix Astragali, the weight ratio of cinnamon extract to Radix Astragali extract is in general from about 3:1 to 1:5, with about 1:1 to 1:2 or about 1:1 to 1:3 being preferred. About equal weight ratio (1:1±10%) of cinnamon to Radix Astragali is more preferred.

The following examples are presented as illustrations, not limitations.

EXAMPLES

Example 1. Effects of Different Water Extracts on Weight Gain

Objectives
Material and Methods

Roots of Radix Astragali were purchased from Beijing Chinese Medicine Pharmacy and 10 g of the roots was incubated in 100 ml water at 80° C. for 2 hours, centrifuged at 5000 rpm for 20 minutes, and then 50 ml of the supernatant was collected and freeze-dried. Water extract of cinnamon was obtain from a commercial product of CINSULIN®. Grape seed extract powder was obtained from MegaNatural®-BP (Polyphenolics), which is a special seed blend from unfermented varietal wine and juice grapes, and was shown to reduce blood pressure in certain situations.

Male C57BL/6J mice (Jackson Laboratories, Sacramento, Calif.) were fed standard laboratory chow (PMI International, Redwood City, Calif.) and housed in plastic shoebox cages in a humidity (60% RH) and temperature (20-22° C.) controlled room. At 10 weeks of age, mice were fed high fat diets (control), or high fat diets supplemented with cinnamon extract (CNMN), astragalus extract (ASTR), and/or grape seed extract (GRP) as shown in the diet composition table (Table 1).

TABLE 1

| Ingredient | CNTRL | CNMN | ASTR | GRP | CNMN + ASTR | GRP + ASTR |
|---|---|---|---|---|---|---|
| Lard Fat | 225.0 | 225.0 | 225.0 | 225.0 | 225.0 | 225.0 |
| Soybean Oil | 25.0 | 25.0 | 25.0 | 25.0 | 25.0 | 25.0 |
| Cholesterol | 0.8 | 0.8 | 0.8 | 0.8 | 0.8 | 0.8 |
| MCC | 50.0 | 48.0 | 48.0 | 48.0 | 48.0 | 48.0 |
| Cinnamon |  | 2.0 |  |  | 1.0 |  |
| *Astragalus* |  |  | 2.0 |  | 1.0 | 1.0 |
| Grape Seed |  |  |  | 2.0 |  | 1.0 |
| Casein | 200.0 | 200.0 | 200.0 | 200.0 | 200.0 | 200.0 |
| Corn Starch | 148.2 | 148.2 | 148.2 | 148.2 | 148.2 | 148.2 |
| Sucrose | 300.0 | 300.0 | 300.0 | 300.0 | 300.0 | 300.0 |
| L-Cystine | 3.0 | 3.0 | 3.0 | 3.0 | 3.0 | 3.0 |
| Choline Bitartrate | 3.0 | 3.0 | 3.0 | 3.0 | 3.0 | 3.0 |
| Mineral Mix | 35.0 | 35.0 | 35.0 | 35.0 | 35.0 | 35.0 |
| Vitamin Mix | 10.0 | 10.0 | 10.0 | 10.0 | 10.0 | 10.0 |
| Total Diet (g) | 1000.0 | 1000.0 | 1000.0 | 1000.0 | 1000.0 | 1000.0 |
| Mice (n) | 10 | 8 | 8 | 8 | 8 | 8 |

Body weight of mice were measured at day 0, 7, 14, 21, and 28. After 4 weeks on the different diets, the mice were anesthetized with isoflurane and exsanguinated under anesthesia by removing blood by heart puncture. Liver, epididymal adipose and kidney were collected and weighed.

Results

FIG. 1 shows the mean body weight vs. time at week 0, 1, 2, 3, and 4 of each group of mice having different diets. Mice having high fat diets supplemented with 0.1% cinnamon extract and 0.1% astragalus extract had significantly less body weight at weeks 2, 3, and 4, with p values of 0.01, 0.0008, and 0.0003 respectively, by unpaired t-tests.

Figure 2:
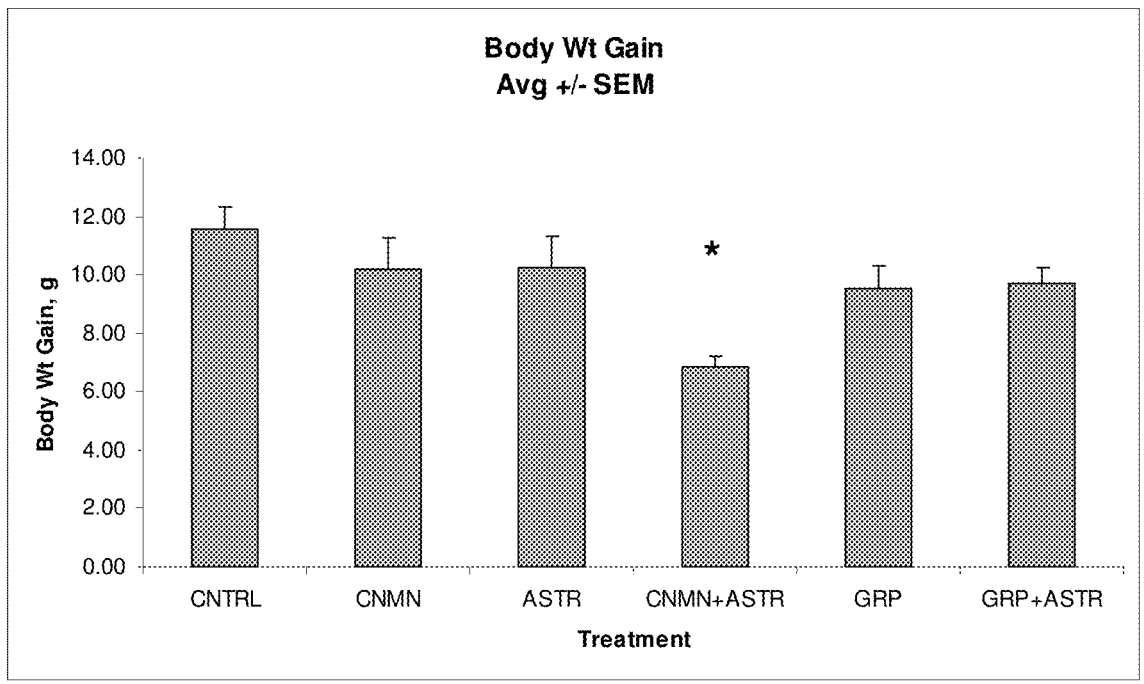
FIG. 2 shows the mean body weight gain of each group of mice having different diets after 4 weeks. Mean body weight gain of each group was calculated by subtracting the mean body weight at day 0 from the mean body weight at 4 weeks. Mice having high fat diets supplemented with 0.1% cinnamon extract and 0.1% astragalus extract had significantly less body weight gain comparing with control (*), by unpaired t-tests.

FIG. 2 shows the mean body weight gain of each group of mice having different diets after 4 weeks. Mice having high fat diets supplemented with 0.1% cinnamon extract and 0.1% astragalus extract had significantly less body weight gain comparing with control (p value of 0.0001).

Figure 3:
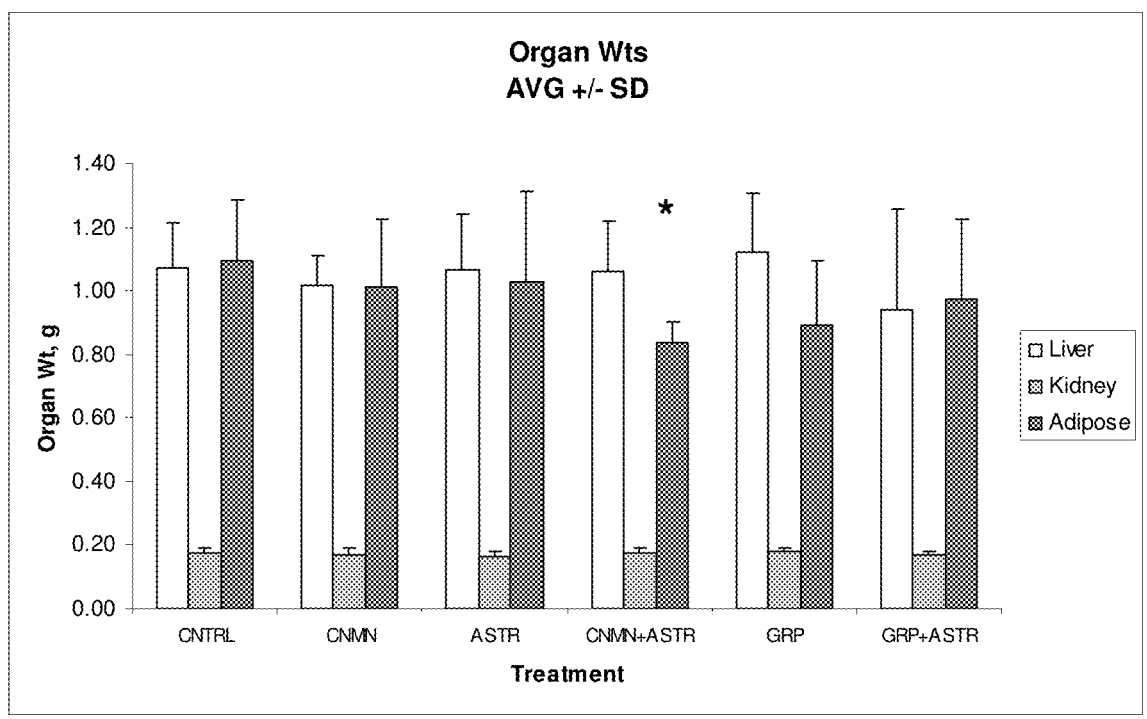
FIG. 3 shows the mean organ weights of liver, kidney, and adipose of each group of mice having different diets after 4 weeks. Mice having high fat diets supplemented with 0.1% cinnamon extract and 0.1% astragalus extract had significantly less epididymal adipose weight comparing with control (*).

FIG. 3 shows the mean weights of liver, kidney and adipose of each group of mice having different diets after 4 weeks. Mice having high fat diets supplemented with 0.1% cinnamon extract and 0.1% astragalus extract had significantly less epididymal adipose weight comparing with control (p value of 0.01).

The results show that mice fed a high fat diet containing 0.1% cinnamon extract and 0.1% astragalus extract (CNMN+ASTR) significantly reduced body weight gain, total body weight, and epididymal adipose weight. Individual extract, i.e., 0.2% cinnamon extract (CNMN) or 0.2% astragalus extract (ASTR), did not have any significant effects on body or organ weights. The results show that the combination of cinnamon extract astragalus extract provides a synergistic effect of reducing weight, and preventing or reducing weight gain. Grape seed extract (GRP) and GRP+ASTR did not have significant effects on body or organ weights.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed:

1. A method for reducing excessive body weight from a mammal subject suffering from excessive weight or overt obesity, comprising the steps of identifying a subject in need thereof, and administering to the subject active ingredients consisting essentially of an effective amount of a water extract of cinnamon bark and an effective amount of a water extract of Radix Astragali, wherein the weight ratio of cinnamon to Radix Astragali is about 1:1.

2. The method according to claim 1, wherein the water extract of cinnamon bark and the water extract of Radix Astragali are administered in a composition containing the two water extracts.

3. The method according to claim 1, wherein the water extract of cinnamon bark and the water extract of Radix Astragali are administered separately.

4. The method according to claim 1, wherein the active ingredients are administered orally.

5. A method for preventing a mammal at risk for gaining excessive weight, comprising the steps of identifying a subject in need thereof, and administering to the subject active ingredients consisting essentially of an effective amount of a water extract of cinnamon bark and an effective amount of a water extract of Radix Astragali, wherein the weight ratio of cinnamon to Radix Astragali is about 1:1.

6. The method according to claim 5, wherein the water extract of cinnamon bark and the water extract of Radix Astragali are administered in a composition containing the two water extracts.

7. The method according to claim 5, wherein the water extract of cinnamon bark and the water extract of Radix Astragali are administered separately.

8. The method according to claim 5, wherein the active ingredients are administered orally.

* * * * *